United States Patent [19]

Sirkar

[11] 4,338,472
[45] Jul. 6, 1982

[54] CATALYTIC HYDROGENOLYSIS OF ALDITOLS TO PRODUCE POLYOLS

[75] Inventor: Amalesh K. Sirkar, Lawrenceville, N.J.

[73] Assignee: Hydrocarbon Research, Inc., Lawrenceville, N.J.

[21] Appl. No.: 227,000

[22] Filed: Jan. 21, 1981

[51] Int. Cl.³ ............................................. C07C 31/22
[52] U.S. Cl. .................................... 568/861; 252/414
[58] Field of Search ............................... 568/861, 863

[56] References Cited

U.S. PATENT DOCUMENTS

| | | | |
|---|---|---|---|
| 2,004,135 | 6/1935 | Rothrock | 578/861 |
| 2,174,651 | 10/1939 | Byrkit | 568/863 |
| 2,456,633 | 12/1948 | Haensel | 252/460 |
| 2,549,416 | 4/1951 | Brooks | 568/881 |
| 2,851,390 | 12/1957 | Gwynn et al. | 568/882 |
| 2,852,570 | 9/1958 | Conradin et al. | 568/861 |
| 2,965,679 | 12/1960 | Conradin et al. | 568/861 |
| 3,481,836 | 12/1969 | Nomura et al. | 568/863 |
| 3,676,364 | 7/1972 | Coates | 568/861 |

FOREIGN PATENT DOCUMENTS

| | | | |
|---|---|---|---|
| 523789 | 4/1956 | Canada | 568/863 |
| 35860 | 1/1965 | German Democratic Rep. | 568/863 |
| 688515 | 3/1953 | United Kingdom | 568/863 |

OTHER PUBLICATIONS

Lange, "Handbook of Chemistry", 10th ed. (1961), pp. 951, 952.

Primary Examiner—Joseph E. Evans
Attorney, Agent, or Firm—Vincent A. Mallare; Fred A. Wilson

[57] ABSTRACT

Alditols such as 15–40 W % sorbitol solution in water are catalytically hydrocracked in a fixed bed catalytic reaction process using an active nickel catalyst to produce at least about 30 W % conversion to glycerol and glycol products. The feedstream pH is controlled to between 7 and 14 by adding a basic promotor material such as calcium hydroxide to prevent damage to the catalyst. Useful reaction zone conditions are 400°–500° F. temperature, 1200–2000 psig hydrogen partial pressure, and liquid hourly space velocity of 1.5 to 3.0. To maintain desired catalyst activity and product yields, the catalyst is regenerated to provide catalyst age within the range of 20–200 hours. The reaction products are separated in distillation steps at successively lower pressures, and unconverted alditol feed is recycled to the reaction zone for further hydrogenolysis to produce 80–95 W % glycerol product. Sorbitol conversion is maintained preferably at between about 30–70 W % by catalyst regeneration following 20 to 200 hours use, comprising washing to remove deposits and heating with hydrogen at 500°–600° F. temperature. Countercurrent flow of feed and hydrogen in the reaction zone can be used if desired, particularly for achieving higher conversion of alditol feed to glycerol products.

11 Claims, 2 Drawing Figures

CATALYTIC HYDROGENOLYSIS OF ALDITOLS TO PRODUCE POLYOLS

BACKGROUND OF INVENTION

1. Field of Invention

This invention pertains to the hydrogenolysis of alditols such as sorbitol to produce glycerol and glycol products using an improved continuous fixed bed catalytic process.

2. Description of Prior Art

The production of glycerol and polyols by hydrogenolysis of sorbitol has been widely studied. Generally, an optimum 30-40 W % of glycerol congeners has been reported in the product obtained from autoclave batch reaction processes. The reaction conditions used are high hydrogen partial pressure of 2000-5000 psig, temperature of 200°-250° C., (392°-482° F.), long residence time of 1.5 hours or more, and use of fine nickel powder catalyst of 100-200 mesh size in the form of a slurry with the feed.

A disclosure regarding hydrogenolysis of sorbitol is provided by Clark in Industrial & Engineering Chemistry, Vol. 50, No. 8 (Aug. 1958), pages 1125-1126. Aqueous solutions containing 40% of 99% D-sorbitol were used with 1% calcium hydroxide promotor and 50% nickel on kieselguhr catalyst suspended in a slurry with the feed in a stirred reactor. Conditions used were 2000-5600 psi hydrogen partial pressure, 215°-245° C. (419°-473° F.) temperature and reaction times up to 400 minutes (6.7 hrs) to produce glycerol, ethylene glycol, propylene glycol, and other more minor products.

U.S. Pat. No. 2,965,679 to Conradin discloses a similar process for producing glycerol and glycols from sugar alcohols using a suspended nickel on kieselguhr catalyst in an autoclave type reactor. Reaction conditions are 200°-300° C. temperature, 500-1000 atmospheres pressure and pH of 8-10, followed by filtration to remove catalyst and separation of the products.

Van Ling et al disclosed in Journal of Applied Chemistry, Vol. 19, 1969, pages 43-45, hydrogenation experiments using slurried catalyst in autoclave reactor on feeds of sucrose, glucose and fructose in methanol-water solution to produce glycerol. Catalyst used was $CuO\text{-}CeO_2\text{-}SiO_2$ with 0-5% $Ca(OH)_2$ addition to feed. Reaction conditions used were 200°-250° C. temperature, 100-300 atmospheres pressure and 10-120 minutes reaction time. Van Ling et al further disclosed in Industrial and Engineering Chemistry, Vol. 9, No. 2, 1970, pages 210-212, a process for hydrogenolysis of sucrose to make glycerol, using two stirred reactors connected in series. The sucrose was mixed with methanol-water solvent and $CuO\text{-}CeO_2\text{-}SiO_2$ catalyst and reacted at 200°-225° C. and 200 atmospheres pressure, after which glycerol can be recovered by multi-stage distillation.

U.S. Pat. No. 3,341,609 to Kasehagen discloses a process for producing glycerol and glycols using Raney nickel catalyst in slurry form at 190°-220° C. and pressures up to about 2000 psig, followed by separation and distillation steps. U.S. Pat. No. 3,471,580 to Hellwig et al discloses that by using a single or multi-stage upflow ebullated bed catalytic reactor at 200°-550° F. temperature and 700-3500 psia hydrogen partial pressure, glycerol and glycols can be produced from saccharides. Examples of the conditions used for converting a sorbitol type feed to glycerol in a single stage reaction were about 375° F. temperature, 1700 psia hydrogen partial pressure, 1.2 liquid hourly space velocity (LHSV), and using nickel on alumina catalyst to produce roughly 50 W % glycerol and 20 W % propylene glycol, with the remainder being methanol, ethanol, isopropanol, and other products.

It is believed that none of these known processes are presently being used commercially to produce glycerol and related products on a continuous basis. Thus, further process improvements in alditol conversion are needed for achieving continuous operations at reduced reaction conditions and increased glycerol product yields are desired, particularly using improved catalysts in fixed bed reactors. By selecting optimum catalyst size, some increase in catalyst age can be achieved before regeneration is needed.

SUMMARY OF INVENTION

The present invention discloses an improved process for continuous fixed catalyst bed reaction for converting alditols such as sorbitol, mannitol, and xylitol by hydrogenolysis to produce glycerol and other polyols products. The fixed-bed type reaction zone, using an improved porous nickel catalyst on an inert support, operates at moderate conditions and short residence times, and provides the inherent advantages of limiting back mixing of the feed and suppressing undesired secondary reactions. This process utilizes as its feedstock solutions of alditols such as sorbitol, mannitol and xylitol, which are catalytically convertible into mainly glycerol and glycol products. Such solutions are either aqueous or can preferably use alcohols or mixtures of water and alcohols. Catalytic hydrogenolysis of such alditols produces a wide range of products which consist principally of glycerol, propylene glycol and ethylene glycol. In fixed bed catalytic reaction process for the hydrogenolysis of alditols, it has been found that improved yields of glycerol can be obtained by maintaining the operating parameters of sorbitol feed concentration, reaction temperature, and catalyst age within specific ranges.

An alkali promotor material, such as calcium hydroxide or sodium hydroxide, is added to the feedstream solution in sufficient concentrations to control the pH of the feedstream and prevent leaching nickel from the catalyst and to enhance the reaction and are usually within the range of 0.1-1.0 W % promotor. The preferred feed material is 15-60 W % sorbitol in water solution for reasons of low cost and good availability.

For high conversion of alditols to continuously produce high yields of at least about 30 W % and preferably 40-60 W % glycerol products, it has been found that the reaction zone operating conditions should be maintained within the range of 400°-510° F. (204°-266° C.) temperature and 1200-2000 psig hydrogen partial pressure. The liquid hourly space velocity (LHSV) should be maintained between about 1.5 and 3.0 volumes of feed per hour per volume catalyst ($V_f/hr/V_c$), at which feed rate the yield of glycerol increases with the concentration of calcium hydroxide promotor between about 0.3 and 1.0 W %. For sorbitol feed, the concentration of sorbitol in aqueous solution in the feedstream should be at least about 15 W % and for best product selectivity results usually should not exceed about 60 W %, with 20-40 W % concentration usually being preferred. Also, the volume ratio of hydrogen gas/liquid in the feedstream should be at least about 1000, at standard conditions, and usually need not exceed about 5000 for achieving good contact between the liquid feed solution and catalyst. The resulting yield of glycerol from the reaction zone is 30–40 W %, with balance being glycols and other minor products.

Under some conditions, to obtain increased conversion of the alditol feed, it is advantageous to provide counter-current flow of the feedstream and hydrogen in the reaction zone. This flow arrangement provides higher hydrogen partial pressure to the downstream portion of the catalyst bed, thus helping the alditol/sugar equilibrium to shift towards alditols.

The catalyst usually used in this continuous fixed bed reaction process is a high activity nickel catalyst on silica or alumina support, containing 30–70 W % nickel, and preferably 50–66 W % porous nickel, and having particle size of 4–12 mesh (U.S. Sieve Series). Good results have been obtained using an improved porous nickel catalyst material containing about 60 W % nickel on kieselguhr clay support in 8–12 mesh size or pellets 3/16 inch diameter × $\frac{1}{8}$ inch length, and having surface area of 150–200 meter$^2$/gm.

Reaction zone conditions preferred for achieving hydrogenolysis and high conversion of alditols to mainly glycerol product are 420°–500° F. temperature and 1400–1800 psig hydrogen partial pressure. The most preferable reaction conditions are 440°–480° F. temperature, 1500–1750 psig hydrogen partial pressure, liquid hourly space velocity within the range of 1.8 to 2.8 volume feed/hr/volume and gas/liquid volume ratio of 1500 to 4500. The sorbitol feed concentration is usually 15–40 W %, in aqueous solution and the desired range of sorbitol conversion to glycerol and glycol products is 40 to 70 W % of feed.

Significant catalyst deactivation usually occurs due to oxidation of the nickel following extended use of at least about 20 hours and usually after 30–200 hours use. However, useful catalyst activity is maintained and also product selectivity is improved by periodic regeneration of the catalyst. For regeneration, the catalyst is preferably washed with a solvent such as water to remove deposits and the contacted with hot reducing gas such as hydrogen passing through it at elevated temperature above the reaction temperature, usually at 400°–600° F. to substantially remove the surface oxidation and vaporize the deposits. Continuous operation of the process is maintained by using two or more reactors which are operated in parallel, with the catalyst beds being used and regenerated alternately, such as at 20–100 hour intervals. Also, it has been found that the regenerated catalyst provides for improved selectivity for desired glycerol products as compared to using fresh catalyst, as undesired secondary cracking reactions are reduced by use of the regenerated catalyst.

Results show that as the concentration of sorbitol in the feed increases, the sorbitol conversion increases the yield of glycerol decreases and the yields of propylene glycol and ethylene glycol are significantly higher. Sorbitol cracking involves a first order kinetics as determined from operations carried out with 25% sorbitol solution feed. However, when the sorbitol concentration in feedstream is increased to say 40%, it shows higher conversion of sorbitol at the same temperature and space velocity at higher initial temperature. Such anomaly apparently occurs because sorbitol hydrogenolysis, especially at high concentrations, appears to be heat sensitive in that the heat evolved during the reaction helps increase the rate of sorbitol cracking. Localized increase in temperature occurs due to slower rate of heat dissipation, which accelerates the hydrogenolysis reactions (which normally occur at higher temperatures) and helps speed up secondary reactions. The activation energy for glycerol from sorbitol being lower than those for ethylene and propylene glycol, the reaction helps in increasing the yield of glycols as sorbitol concentration increases. It is therefore concluded that both lower initial sorbitol concentration and lower initial temperature maximize the yield of glycerol, whereas higher sorbitol concentration and higher initial temperature helps maximize the production of glycols. It may be noted that use of solvent as a feed diluent for sorbitol hydrogenolysis that vaporizes easily; i.e., boils at low temperature, helps maximize the yield of glycerol, whereas a solvent that slows down the rate of heat dissipation would be more suitable for glycol production.

It has been found from yield data on sorbitol hydrogenolysis that the yields of propylene glycol, butanols and mannitol increase with aging of the nickel catalyst. The compounds which are produced in significant quantities and undesirable are polyglycerols and the sugars of various alditols (erythritol, xylitol, arabinol). The sugars are produced to maintain the equilibrium with their alditols, whereas the polyglycerols are produced by thermal dehydration of glycerol at higher temperature. Formation of polyglycerols reduce the net yield of glycerol and the sugars reduce the yield of alditols and hence other useful products from alditols.

Reactor types and reaction conditions used for maximizing the yield of glycerol and other useful products, and for minimizing the yields of polyglycerols and the sugars which tend to build up in the system to their equilibrium concentration levels are plug flow type catalytic reactor to avoid backmixing to prevent secondary and undesirable reactions and use high space velocity, such as above about 2.0 volume feed/hr/volume reactor. Higher space velocity means lower conversion of feed per pass in the reactor, but unconverted sorbitol can be separated in a recovery step and recycled back to the reactor. Higher space velocity (or shorter residence time) helps in minimizing the formation of undesirable products from secondary reactions.

Following catalytic reaction of the feed, the reaction zone effluent stream is pressure-reduced, demineralized and passed to recovery steps involving distillation steps for removing all products such as alcohols, water, and glycols having lower boiling temperature than desired glycerol product for achieving increased recovery of glycerol and other desired products. Following removal of volatile materials, a major portion of the heavy bottom liquid stream containing unconverted sorbitol feed is preferably recycled to the reaction zone for further catalytic reaction and conversion to mainly glycerol product. Yield from the process following distillation is 40–50 W % glycerol, based on sorbitol feed, with the balance being glycols and other minor products.

The present process for catalytic hydrogenation of alditols to produce glycerols provides the advantageous characteristics of permitting improved continuous operation in a down-flow fixed-bed catalytic reactor configuration, and uses a very active stabilized nickel catalyst having selected particle size and improved selectivity following regeneration. It also uses lower hydrogen partial pressure and higher liquid hourly space velocity (LHSV) than previous known processes. These process characteristics are combined in this invention to provide a sorbitol hydrogenolysis process which produces superior results, and is more suitable for commercial use than previously known processes.

DESCRIPTION OF PREFERRED EMBODIMENTS

Figure 1:
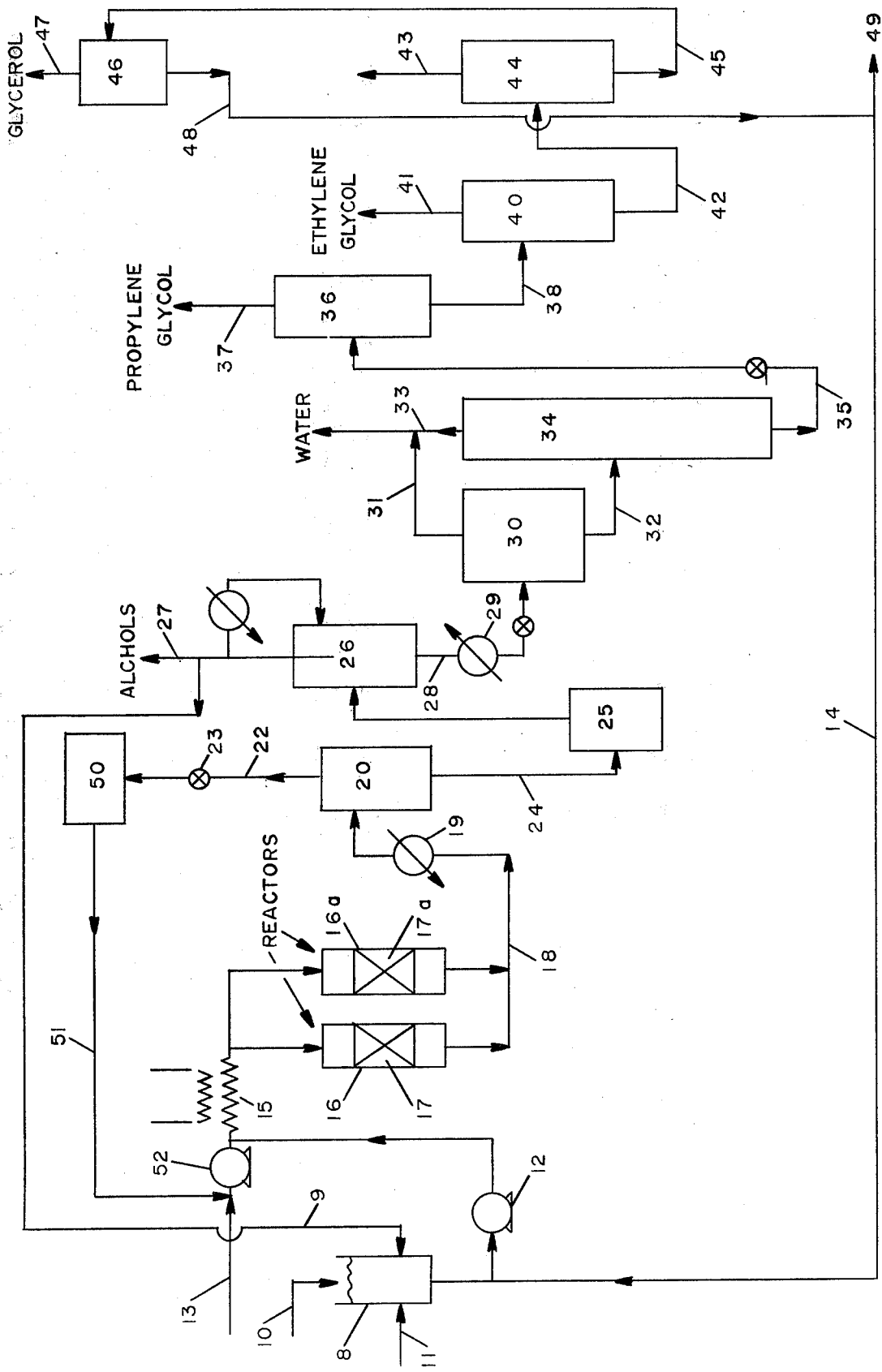
FIG. 1 is a schematic drawing showing the sorbitol hydrogenolysis process, including catalytic reaction and various product distillation steps.

As shown in FIG. 1, a 20-50 W % sorbitol solution such as obtained from glucose is provided in water solution at 10. The solution pH is adjusted to prevent any substantial leaching of nickel from the catalyst, and will usually be controlled within the range of 7-14 by addition of an alkali promotor at 11, preferably 0.1-1 W % calcium hydroxide. The alkali promotor used should all remain in solution, as any excess promotor can settle on the catalyst and reduce its activity. The resulting feedstream solution mixed at 8 is pressurized at 12 and passed together with fresh hydrogen from 13 through preheater 15, where it is heated by any convenient means to about 400° F. The feedstream is usually mixed with a recycle stream 14 containing unconverted sorbitol, some $C_4-C_5$ alditols and some polyglycerols and then passed into reactor 16.

The reactor 16 contains a fixed bed of particulate catalyst 17, and the liquid feed and hydrogen gas are preferably passed downwardly through the bed in intimate contact with the catalyst. The reactor is maintained at elevated temperature and pressure conditions within the range of 430°-490° F. temperature and 1200-2000 psig hydrogen partial pressure. The sorbitol solution feed rate or liquid hourly space velocity should be at least about 1.8 and usually need not exceed about 2.8 Vf/hr/Vc for good hydrogenolysis reaction results. The hydrogen gas/liquid volume ratio should be maintained at least about 1000 for good contact between the liquid solution and catalyst, and usually need not exceed about 5000. Also, the feed liquid mass velocity is usually maintained within the range of 2000-3000 lb/hr/ft$^2$. The sorbitol is reacted and converted to at least about 30 W % glycerol along with some glycol products.

The catalyst used in reactor 16 is a special reduced and stabilized high nickel catalyst on kieselguhr support, containing 60-66 W % nickel and having 4-12 mesh (U.S. Sieve Series) particle size (0.187-0.066 inch). The catalyst becomes more active with use up to a limiting age, due to use of a "stabilized" catalyst, which is a catalyst that is covered with a mono-molecular layer of carbon dioxide to prevent spontaneous oxidation of the highly active nickel when the catalyst is exposed to the air during charging it into the reactor. In industrial practice, the catalyst is usually prereduced in situ with hydrogen to achieve maximum conversion of sorbitol to glycerols. Limiting the pretreatment step to about two hours is usually sufficient, since a catalyst with too high an initial activity may cause carbon deposition on the catalyst.

Because the catalyst becomes deactivated by oxidation during extended use and must be regenerated to maintain useful sorbitol conversion levels, dual catalyst reactors are provided in parallel for alternate use. After an operation period of at least about 20 hours of catalyst use, so that the conversion of sorbitol decreases to below about 30 W %, and usually not exceeding about 200 hours, the feed is switched from reactor 16 to alternate reactor 16a containing catalyst bed 17a. The used catalyst 17 can be regenerated by first washing with water or a water-methanol solution to remove reaction products, and then contacting the catalyst with hydrogen at 500°-650° F. temperature and atmospheric pressure for 2-10 hours duration to remove oxidation. Catalyst regeneration is preferably conducted after 24-150 hours operation by washing with 25% water—75% methanol solution for about 4 hours, followed by contacting the catalyst with flowing hydrogen at 550°-600° F. temperature and atmospheric pressure for about 8 hours.

The reactor effluent stream at 18 is cooled in heat exchanger 19 against a suitable fluid such as water, and/or other process stream which requires heating e.g. a process hydrogen stream. The cooled stream is passed to high pressure separator 20, wherein the fluid is separated into an overhead gas stream 22 and bottoms liquid stream 24. Overhead stream 22 contains mainly hydrogen and some methane, and is pressure-reduced at 23 and passed to hydrogen purification unit 50. Here the gas is purified to about 90 V % hydrogen and recycled as stream 51 through compressor 52 to reactor 16 for reuse.

Separator bottoms stream 24 is demineralized at 25 to remove calcium or sodium ions added at 11. The demineralized liquid is passed to alcohol separation column 26 at about atmospheric pressure where the monohydroxy alcohols are removed as stream 27. Bottoms stream 28 is preheated at 29 and passed to low pressure separator 30, from which overhead water vapor stream 31 is withdrawn. The bottoms stream 32 is passed to water distillation column 34 from which overhead water vapor stream 33 joins stream 31. Operation at vacuum pressure is usually not necessary as the temperature at the lower end of columns 26 and 34 does not exceed the decomposition temperature of about 400° F. for glycerol when operated at atmospheric pressure.

Liquid products 35 from the bottom of water column 34 is pressure reduced to about 50 to 200 mm Hg pressure and fed to propylene glycol recovery column 36 to ensure that the temperature at the bottom of that column does not exceed the glycerol decomposition temperature (about 400° F.). Propylene glycol of about 92 W % concentration is recovered in overhead stream 37 with the impurities being mostly diols. The bottoms 38 from the propylene glycol column 36 is fed to ethylene glycol recovery column 40, which is also operated at vacuum pressure. The vacuum pressure maintained at the bottom of column 40 is slightly lower than in the propylene glycol column 36 to prevent the temperature exceeding the glycerol decomposition temperature. High purity ethylene glycol is recovered as overhead stream 41, and the bottoms stream 42 is passed to crude glycerol column 44 to recover remaining traces of diols, triols and glycerols at 43. Bottoms stream 45 is passed to final distillation step 46 in order to obtain high purity glycerol.

Because it has been found that slow vacuum distillation procedures for glycerol usually allows the undesirable reactions and formation of poly-glyceride products, it is advantageous to provide such distillation at minimum temperature, preferably not exceeding about 400° F. to limit such undesired side reactions. Accordingly, thin film type evaporation is preferably provided for distillation step 46, such as by a falling film or wiped film-type evaporator. This final distillation step preferably uses thin film evaporation at lower vacuum pressure of about 10-30 mm Hg to limit the temperature to not exceeding about 400° F. and thus minimize any undesirable side reactions. A high purity (98 to 99%) glycerol product stream 47 can be obtained as the overhead from the thin film evaporator 46. The bottoms stream 48 from evaporator unit 46 contained $C_4$-$C_6$ alditols, $C_4$-$C_6$ aldoses and polyglycerols. A portion 14 of stream 48 is recycled back to the sorbitol conversion reactor 16, for further reaction, while the remainder is removed as a heavy purge stream 49.

If desired, a portion 9 of alcohols stream 27 can be recycled to mixing step 8 to provide at least a portion of the solvent liquid for the feedstream. Because of the increased solubility of hydrogen in water in the presence of alcohol, the total operating pressure can be reduced significantly, thus reducing capital costs for the process.

Figure 2:
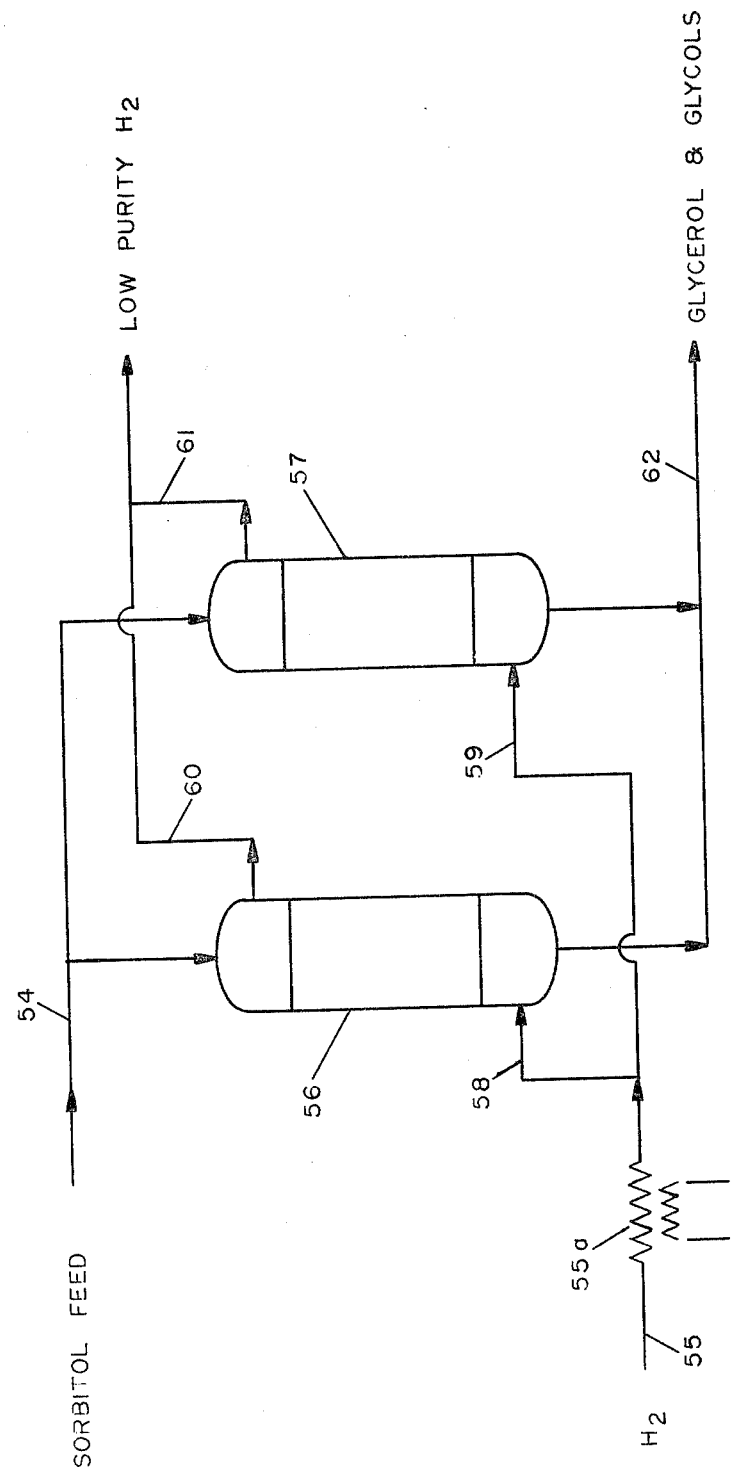
FIG. 2 is a schematic drawing showing counter-current flow of sorbitol feed and hydrogen in the reactor.

When it is desired to achieve higher conversion of the sorbitol feed to glycerol and glycol products, it is advantageous to provide for some hydrogen flow countercurrent with the feedstream in the reactor catalyst bed, as generally shown by FIG. 2. Such countercurrent flow of sorbitol feed and hydrogen is sometimes desirable rather than concurrent flow because higher hydrogen partial pressure is provided in the downstream section of the reactor catalyst bed to reduce the degree of polymerization of glycerol and to allow alditol-sugar equilibrium to be shifted towards production of alditols. Also, some recycle hydrogen can be introduced along with the feed. Useful reactor types are either a countercurrent-flow packed bed reactor, shown in FIGS. 1 and 2, or a countercurrent plug flow reactor where the feed liquid contains the catalyst in the form of finely divided suspended particles.

The preheated sorbitol feedstream at 200°-400° F. temperature at 54 is passed to either catalytic reactor 56 or 57, while the catalyst in the alternate reactor is being regenerated. Hydrogen stream 55 is heated as needed at 55a and stream 58 or 59 is passed through the catalyst bed in use countercurrent to the sorbitol feed. The hydrogen superficial velocity should be such that the bed is not flooded by downcoming liquid, and hydrogen is removed at 60 or 61 and passed to purification step 50. From the reactor, the converted effluent stream 62 containing glycerol, glycols and alcohols is passed to further processing steps as described for the FIG. 1 embodiment to recover glycerol product.

To take fuller advantage of the countercurrent flow arrangement for the feed and hydrogen streams, the sorbitol hydrogenolysis reaction could be carried out in multiple reaction stages with higher hydrogen partial pressures being provided in the succeeding stages. It may be noted that with such a countercurrent flow arrangement for sorbitol feed and hydrogen, hydrogenolysis operations could be carried out at moderately lower space velocity than in the cocurrent flow arrangement.

This invention is further illustrated by the following examples, which should not be construed as limiting the scope of the invention.

EXAMPLE 1

Experimental runs were made using sorbitol-water feed solution containing various concentration of sorbitol between about 25 and 45 W % in a small fixed bed reactor containing a catalyst bed composed of 60 W % porous nickel on kieselguhr support and having 4-12 mesh particle size (0.074 to 0.173 inch equivalent diameter). Runs with the smaller size crushed catalyst were made in a reactor 0.464 inch inside diameter by 12 inches high, and runs with larger pellet catalyst were made in a reactor 1.0 inch diameter by 15 inches high. Results of runs made at space velocity of 2.0 Vf/hr/Vc and catalyst age up to 16 hours are shown in Table 1, which shows the effect of sorbitol feed concentration and reactor temperature on the weight percent of sorbitol and yield of glycerol.

TABLE 1

| Run No. | Sorbitol Feed Concent. W% | Reactor Temp °F. | Catalyst Size, Inch | Sorbitol Yield | Glycerol Yield* |
|---|---|---|---|---|---|
| 1 | 25 | 445 | 0.074 | 0.18 | 0.413 |
| 2 | 36 | 445 | 0.074 | 0.375 | 0.326 |
| 3 | 44 | 445 | 0.074 | 0.531 | 0.191 |
| 4 | 25 | 500 | 0.074 | <0.01 | 0.095 |
| 5 | 36 | 500 | 0.074 | <0.01 | 0.11 |
| 6 | 44 | 500 | 0.074 | <0.01 | 0.131 |
| 7 | 25 | 445 | 0.173 | 0.348 | 0.712 |
| 8 | 36 | 445 | 0.173 | 0.502 | 0.54 |
| 9 | 44 | 445 | 0.173 | 0.613 | 0.303 |
| 10 | 25 | 500 | 0.173 | 0.106 | 0.25 |
| 11 | 36 | 500 | 0.173 | 0.044 | 0.26 |
| 12 | 44 | 500 | 0.173 | 0.016 | 0.27 |

*Yield of glycerol is expressed in lb/lb sorbitol converted.

These results show two opposite trends regarding reaction temperature effect as sorbitol feed concentration increases. At lower reactor temperature (445° F.) sorbitol conversion decreases as sorbitol feed concentration increases, whereas at higher temperature (500° F.) sorbitol conversion increases with increase in sorbitol feed concentration. Similarly, glycerol yield decreases at lower temperature, but increases at higher temperature with increase in sorbitol feed concentration. A probable explanation for the opposite yield trend is that sorbitol hydrogenolysis is either mildly exothermic or highly exothermic, depending on the nature of the products (glycerol and ethylene glycol production reactions are mildly exothermic whereas propylene glycol production is highly exothermic). It appears that at lower reaction temperature the ratio of heat evolved and heat addition or removal rate was such that conversion rate decreased with increase in feed concentration. At higher temperature, however, the ratio was such that exothermicity helped accelerate the hydrogenolysis rate, thus producing either the same or somewhat higher conversion with increase in feed concentration. Glycerol yield essentially reflects the trend of sorbitol conversion since it is the major product in the hydrogenolysis process.

EXAMPLE 2

The effect of catalyst particle size on sorbitol conversion and glycerol yield at reactor temperature of 500° F. and space velocity of 2.0 Vf/hr/Vc for varying catalyst bed heights is shown in Table 2.

TABLE 2

| Run No. | Catalyst Equivalent Diameter Inch | Catalyst Age, hr | Catalyst Bed Height, Inch | Glycerol Yield* |
|---|---|---|---|---|
| 1 | 0.075 | 60 | 8 | 0.1 |
| 2 | 0.125 | 60 | 8 | 0.118 |
| 3 | 0.175 | 60 | 8 | 0.133 |
| 4 | 0.075 | 120 | 8 | 0.114 |
| 5 | 0.125 | 120 | 8 | 0.108 |
| 6 | 0.175 | 120 | 8 | 0.095 |

TABLE 2-continued

| Run No. | Catalyst Equivalent Diameter Inch | Catalyst Age, hr | Catalyst Bed Height, Inch | Glycerol Yield* |
|---|---|---|---|---|
| 7 | 0.075 | 16 | 6 | 0.13 |
| 8 | 0.125 | 16 | 6 | 0.186 |
| 9 | 0.175 | 16 | 6 | 0.255 |
| 10 | 0.075 | 120 | 6 | 0.136 |
| 11 | 0.125 | 120 | 6 | 0.135 |
| 12 | 0.175 | 120 | 6 | 0.122 |

*Yield of glycerol in lb/lb sorbitol converted.

From the Table 2 results it is seen that in general the yield of glycerol increases with increase in the catalyst equipment diameter when the catalyst is rather fresh or aged less than about 100 hours. However, this glycerol yield trend is reversed as the catalyst becomes aged to above about 100 hours. Also, the conversion of sorbitol showed the same trend, i.e. lower conversion for larger catalyst particle diameter irrespective of the degree of catalyst aging.

EXAMPLE 3

Because it was found that catalyst activity for sorbitol hydrogenolysis declined after at least about 20 hours operation, further experiments were run to determine allowable catalyst age before regeneration is needed to maintain desired glycerol product yields. Runs were made with 25 W % sorbitol in water solution using 60% nickel on kieselguhr catalyst having particle sizes of 0.074 inch and 0.173 inch equivalent diameter. During regeneration, the catalyst was washed with a solvent solution containing 25 W % water and 75 W % methanol, followed by contacting the catalyst with hydrogen at 575° F. at atmospheric pressure and hydrogen flow rate of 0.125 ft³/min for 4 hours. The general relationships observed between catalyst age, catalyst particle size and glycerol yield up to a catalyst age of about 120 hours for typical space velocity of 2.0 Vf/hr/Vc is shown in Table 3.

TABLE 3

| Run No. | Catalyst Age, Hrs | Catalyst Size Inch | Reactor Temperature °F. | Bed Height Inch | Glycerol Yield* |
|---|---|---|---|---|---|
| 1 | 20 | 0.074 | 445 | 8 | 0.413 |
| 2 | 70 | 0.074 | 445 | 8 | 0.411 |
| 3 | 120 | 0.074 | 445 | 8 | 0.421 |
| 4 | 20 | 0.173 | 445 | 6 | 0.70 |
| 5 | 70 | 0.173 | 445 | 6 | 0.546 |
| 6 | 120 | 0.173 | 445 | 6 | 0.369 |
| 7 | 20 | 0.074 | 500 | 8 | 0.095 |
| 8 | 70 | 0.074 | 500 | 8 | 0.1 |
| 9 | 120 | 0.074 | 500 | 8 | 0.114 |
| 10 | 20 | 0.173 | 500 | 6 | 0.246 |
| 11 | 70 | 0.173 | 500 | 6 | 0.176 |
| 12 | 120 | 0.173 | 500 | 6 | 0.123 |

*Lb/Lb sorbitol converted.

From Table 3 it is seen that with increased catalyst aging the yield of glycerol increases for the smaller (crushed) catalyst particle size, whereas the glycerol yield decreases for the larger (pellet) catalyst size. In commercial operations it is expected that smaller size catalyst can be used at ages exceeding 120 hours, and for larger pellet size catalyst its age should be limited to about 100 hours before regeneration. However, both sizes of catalyst are suitable for achieving desirable yields of glycerol product.

Thus, it is seen that in general for catalyst particles larger than about 0.150 inch equivalent diameter, regeneration should occur after about 100 hours of use. However, for smaller catalyst particles, increased catalyst age can be used up to about 200 hours. Such catalyst sizes and age before regeneration procedure desirably maintains sorbitol conversion between about 40 and 70 W % of the sorbitol feed, and the recycle of unconverted sorbitol fraction permits producing 40–50 W % yield of glycerol based on sorbitol converted. Also, it is noted that the catalyst selectivity for glycerol product is improved when using regenerated catalyst instead of fresh catalyst.

Although this invention has been described in terms of the accompanying drawings and preferred embodiment, it is recognized that many modifications of the invention can be made without departing from the spirit and scope thereof, which is defined solely by the following claims.

What I claim is:

1. A process for metallic catalytic hydrogenolysis of an alditol solution to produce glycerol, comprising the steps of:
    (a) providing a feedstream solution containing at least about 15 W % alditol and adding an alkaline promotor material to the feedstream sufficient to provide a pH within the range of 7–14;
    (b) preheating the feed solution and hydrogen gas to at least about 200° F. temperature, and introducing the heated feedstream mixture into a fixed bed reaction zone containing a particulate high activity stabilized nickel catalyst containing 50-65 W % porous nickel on silica support and having 4–12 mesh (0.132–0.066 inch) particle size (U.S. Sieve Series);
    (c) maintaining the reaction zone conditions within the range of 400°–510° F. temperature, 1200–2000 psig hydrogen partial pressure and 1.5–3.0 liquid hourly space velocity (LHSV), and containing the catalyst age by regeneration following at least about 20 hours use when said catalyst is washed with a water-methanol solution to remove deposits and then contacted with flowing hydrogen at 500°–650° F. temperature for at least about 2 hours for achieving at least about 30 W % conversion of the alditol to glycerol and glycol products;
    (d) withdrawing from the reaction zone a stream containing glycerol and glycols and phase separating said stream into a gaseous portion and a liquid portion;
    (e) distilling said liquid portion to remove alcohols and water;
    (f) distilling the remaining stream at sub-atmospheric pressure to remove glycols and produce higher purity glycerol product, and a heavy bottoms liquid stream containing unconverted alditols; and
    (g) recycling at least a portion of said bottoms stream to the reaction zone for further catalytic conversion of alditols to produce mainly glycerol product.

2. The process of claim 1, wherein the feedstream contains 20-60 W % sorbitol in aqueous solution, the reaction zone conditions are maintained within the range of 440°–480° F. temperature, 1400–1900 psig hydrogen partial pressure, 2.0–2.7 liquid hourly space velocity, and said nickel catalyst age is maintained at between 20–200 hours by washing said catalyst with a water-methanol solution to remove deposits and then contacting the catalyst with flowing hydrogen at 550°–600° F. temperature for at least about 2 hours, and wherein the sorbitol feed solution is converted about 30-70 W % to yield mainly glycerol product with the remainder being polyols.

3. The process of claim 1, wherein the promoter added to the feedstream in (a) is calcium hydroxide solution comprising about 0.1 to 2.0 W % of the feedstream.

4. The process of claim 1 wherein dual catalytic reaction zones are provided in parallel to permit continuous operations by using one reaction zone while regenerating the catalyst in the other zone whenever the alditol conversion therein declines to below about 40 W %.

5. The process of claim 1, wherein alcohols removed at step (e) are recycled to help provide the feedstream solution in step (a).

6. The process of claim 1, wherein glycerol product separation at step (f) is achieved by vacuum distillation at 10-60 mm of mercury pressure to remove unconverted alditols and produce 80-95 W % purity glycerol product.

7. The process of claim 1, wherein the final distillation step utilizes thin film type evaporation at 10-60 mm mercury pressure to provide a distillation temperature not exceeding about 400° F. to minimize undesired side reactions therein.

8. The process of claim 1, wherein the feedstream and hydrogen are passed in countercurrent flow through the catalytic reaction zone.

9. The process of claim 2, wherein the catalyst particle size is within range of 0.060-0.150 inch equivalent diameter, and said catalyst is regenerated after about 200 hours use by first washing with a water-methanol solution to remove reaction products and then contacting the catalyst with flowing hydrogen at 500°-650° F. temperature and atmospheric pressure for 2-10 hours to remove oxidation.

10. A process for metallic catalytically converting sorbitol solution to produce mainly glycerol product, comprising the steps of:
   (a) providing a feedstream containing 20-50 W % sorbitol in aqueous solution;
   (b) adding calcium hydroxide promotor between about 0.1 and 1.0 W % to the feedstream to provide a pH within the range of 7-14;
   (c) preheating the feed solution together with hydrogen gas to at least about 200° F., and introducing the heated feedstream mixture into a fixed-bed reaction zone containing a particulate high activity stabilized nickel catalyst containing 50-65 W % porous nickel on silica support and having a 4-12 mesh (0.132-0.066 inch) particle size (U.S. Sieve Series), said catalyst being regenerated after 200 hours use by washing it with a water-methanol solution to remove reaction products and then contacting said catalyst with flowing hydrogen at 550°-600° F. temperature and atmospheric pressure for 2-10 hours to remove oxidation;
   (d) maintaining the reaction zone conditions within the range of 440°-480° F. temperature, 1400-1900 psig hydrogen partial pressure, 2.0-2.7 liquid hourly space velocity (LHSV) and catalyst age of 20-200 hours for achieving 30-70 W % conversion of the sorbitol to yield mainly glycerol with the remainder being polyols;
   (e) withdrawing from the reaction zone a stream containing glycerol and glycol products and phase separating said stream into a gaseous portion and liquid portion;
   (f) distilling said liquid portion to remove alcohols, water and glycols;
   (g) distilling the remaining stream in a vacuum distillation step maintained at 10-60 mm Hg pressure to remove unconverted alditols and produce 40-90 W % purity glycerol product, and a heavy bottoms liquid stream containing unconverted sorbitol; and
   (h) recycling at least a portion of said bottoms stream to the reaction zone for further catalytic conversion of sorbitol to produce mainly glycerol product.

11. The process of claim 10, wherein the catalyst particle size is 0.150 to 0.200 inch equivalent diameter and the catalyst is regenerated after 30-150 hours to provide improved selectivity for glycerol product.

* * * * *